United States Patent [19]

Motola et al.

[11] Patent Number: 5,024,997
[45] Date of Patent: Jun. 18, 1991

[54] PALATABLE IBUPROFEN SOLUTIONS

[75] Inventors: Solomon Motola, Marlton; Gary R. Agisim, Cherry Hill; Annabelle Mogavero, Medford, all of N.J.

[73] Assignee: American Home Products Corporation, New York, N.Y.

[21] Appl. No.: 542,453

[22] Filed: Jun. 22, 1990

[51] Int. Cl.$^5$ ............... A01N 43/04; A01N 37/10; A01N 25/00
[52] U.S. Cl. ................... 514/58; 514/570; 514/781; 514/974
[58] Field of Search ............... 514/58, 570, 781, 974

[56] References Cited

U.S. PATENT DOCUMENTS

| | | | |
|---|---|---|---|
| 4,361,580 | 11/1982 | Peck et al. | 424/287 |
| 4,684,666 | 8/1987 | Haas | 514/557 |
| 4,727,064 | 2/1988 | Pitha et al. | 514/558 |
| 4,788,220 | 11/1988 | Mody et al. | 514/557 |
| 4,916,161 | 4/1990 | Patell | 514/570 |
| 4,952,565 | 8/1990 | Zmitek et al. | 514/58 |

FOREIGN PATENT DOCUMENTS 0274444  7/1988  European Pat. Off. .

OTHER PUBLICATIONS

CA 111(3): 23899z–Markarian et al.
CA 112(12): 104681v–Menard et al.
F. A. Menard et al, "Potential Pharmaceutical Applications of a New Beta Cyclodextrin Derivative", Drug Development and Industrial Pharmacy, 14(11), 1529–1547 (1988).
Orienti, Isabella et al, "Availability of NSAIDH β-Cyclodextrin Inclusion Complexes", Arch. Pharm. (Weinheim) 322, 207–211 (1989).

Primary Examiner—Stanley J. Friedman
Attorney, Agent, or Firm—John W. Routh

[57] ABSTRACT

Palatable ibuprofen aqueous base solutions are described which contain dissolved therein ibuprofen and hydroxypropyl beta cyclodextrin, which form an inclusion complex, and sweeteners to mask the sour taste common to organic acids.

5 Claims, No Drawings

PALATABLE IBUPROFEN SOLUTIONS

FIELD OF INVENTION

This invention relates to palatable ibuprofen aqueous base solutions which contain dissolved therein ibuprofen, hydroxypropyl beta cyclodextrin and a sweetening agent. Such solutions have utility in pharmaceutical preparations for oral administration.

BACKGROUND OF THE INVENTION

Liquid ibuprofen compositions for oral administration are known in the art. One approach to such a formulation is to suspend the finely divided ibuprofen, which is essentially insoluble in water, in an aqueous medium with suspending agents and sweetening agents to mask the bitter taste of any dissolved ibuprofen.

One such composition is described in U.S. Pat. No. 4,684,666 as a stabilized liquid ibuprofen syrup suitable for oral administration comprising from 50 to 400 mg of ibuprofen per 5 ml of syrup, the ibuprofen being suspended in an aqueous liquid having more than 50% by weight of a polyhydric alcohol bodying agent, a sweetening agent and a pH of higher than 7.0 and below 7.7. Another such composition is described in U.S. Pat. No. 4,788,220 wherein the ibuprofen is maintained in suspension by the primary suspending agents xanthan gum, microcrystalline cellulose, sodium carboxymethyl cellulose and polysorbate 80, wherein the ibuprofen is taste-masked with sucrose and sorbitol solution and the pH is maintained at about 3.5 to 5. Another approach is to form a salt of ibuprofen with, for example, aluminum as described in U.S. Pat. No. 4,361,580. Such aluminum ibuprofen salts, which are essentially tasteless are not soluble in water and are also formulated with suspending agents and sweeteners.

PRIOR ART

Ibuprofen complexes with substituted cyclodextrins are known in the art. For example, U.S. Pat. No. 4,727,064 entitled "Pharmaceutical Preparations Containing Cyclodextrin Derivatives", describes pharmaceutical preparations which are socalled inclusion complexes of a drug with a substantially low water solubility and an amorphous, water-soluble cyclodextrinbased mixtures, the cyclodextrin based mixtures being prepared from alpha-, beta, or gamma-cyclodextrin by non-selective alkylation with, for example, epoxides to yield many components. The inclusion complexes are said to result in an improved solubility of the drug and more efficient absorption of the drug by the body. Because of its extensive discussion of cyclodextrin and its inclusion complexes, U.S. Pat. No. 4,727,064 is incorporated by reference herein in its entirety. One cyclodextrin derivative disclosed is hydroxypropyl beta cyclodextrin with a degree of substitution of about 7.

An article appearing in "Drug Development And Industrial Pharmacy", 14(11), 1529–1547 (1988) by F. A. Menard et al entitled "Potential Pharmaceutical Applications of a New Beta Cyclodextrin Derivative" discloses an inclusion complex of ibuprofen and hydroxyethyl beta cyclodextrin.

SUMMARY OF THE INVENTION

According to this invention, novel palatable ibuprofen aqueous base solutions are provided which contain dissolved therein ibuprofen, hydroxypropyl beta cyclodextrin and a sweetening agent which can be formulated into clear solutions for oral administration. The aqueous base solutions contain about 2% to 5% weight by volume of ibuprofen, about 20% to about 70% weight by volume of at least one taste masking sweetening agent, about 22% to about 75% weight by volume of hydroxypropyl beta cyclodextrin, and water qs to 100% by volume of the solution. The hydroxypropyl beta cyclodextrin has a degree of hydroxypropyl substitution of about 6 to about 7.5 and the weight ratio of ibuprofen to hydroxypropyl beta cyclodextrin is 1:11 to 1:15. The aqueous base solutions have a pH of about 3 to 5.

DETAILS OF THE INVENTION

The palatable ibuprofen aqueous base solutions of the invention can be formulated into orally administrable liquid dosage forms containing about 40 mg to about 200 mg of ibuprofen per teaspoon (5 ml) of formulation, preferably about 100 mg/5 ml.

Such orally administrable liquid dosage forms can additionally contain other cough/cold medicinal agents including pseudoephedrine hydrochloride, dextromethorphanhydrobromide, and diphenhydramine hydrochloride. Such additional medicinal agents can be of any national formulary or USP grades.

Preservatives and coloring and flavoring agents can be added as desired. The other ingredients can be any national formulary or USP grades.

Ibuprofen is available commercially from Ethyl Corporation, Baton Rouge, Louisiana in an average particle size of 40 microns.

Hydroxypropyl beta cyclodextrin having a degree of hydroxypropyl substitution of 6 to 7.5 is available commercially from the American Maize Company.

Sweeteners useful in the palatable ibuprofen aqueous base solutions of the invention include sucrose, sorbitol, sorbitol solution, sodium saccharin, glycerin, aspartame and the like. The sweeteners are used primarily to mask the acidic or sour taste of the ibuprofen, which is common to organic acids, as distinguished from the normal bitter taste of ibuprofen, since this bitter taste is eliminated by the inclusion complex formed by the ibuprofen with the hydroxypropyl beta cyclodextrin.

The invention is further described by reference to the following examples.

EXAMPLE 1

An ibuprofen formulation in accordance with this invention was prepared having the following composition.

| Ingredients | % w/v | g/500 ml |
| --- | --- | --- |
| Part I | | |
| Purified Water Deionized, USP | 24.00 | 120.00 |
| Hydroxypropyl-Beta-Cyclodextrin (D.S. = 7) | 24.00 | 120.00 |
| Ibuprofen | 2.00 | 10.00 |
| Part II | | |
| Purified Water Deionized, USP | 19.00 | 95.00 |
| Sodium Benzoate, NF | 0.25 | 1.25 |
| Sodium Saccharin, USP | 0.25 | 1.25 |
| Disodium Edetate, USP | 0.05 | 0.25 |
| Sucrose, NF | 38.00 | 190.00 |
| Glycerin, USP | 10.00 | 50.00 |
| Sorbitol Solution, USP | 10.00 | 50.00 |
| Tropical Citrus Flavor | 0.30 | 1.50 |
| FD & C Blue #1 (0.1% Aq. Soln) | 0.15 | 0.75 |
| FD & C Red #40 | 0.47 | 2.35 |

| Ingredients | % w/v | g/500 ml |
|---|---|---|
| (10% Aq. Soln) | | |
| Part III | | |
| Purified Water Deionized, USP | q.s to 100 ml | q.s to 500 ml |

A 120 gram portion of the water was weighed into a first beaker fitted with a Lightnin mixer and steam bath and the hydroxypropyl beta cyclodextrin was added and dissolved therein. The solution was heated to 50° C. while mixing and the ibuprofen was added. Mixing was continued until the solution was clear while maintaining 50° C. The mixture was then cooled to 25° C. while mixing.

Into a separate jacketed container fitted with a Lightnin mixer, 95 grams of water were added and heated to 70° while mixing. To the hot water were added and dissolved the sodium benzoate, sodium saccharin, disodium edetate and sucrose and the solution was then cooled to 25° C. while mixing. There were then added with mixing the ibuprofen/cyclodextrin solution from the first beaker, the glycerin, sorbitol solution, flavor and color solutions. The batch was mixed for ten minutes, water was added to adjust the volume to 500 milliliters and mixing was continued for an additional ten minutes.

The final solution had a pH of 4.10 and was a clear deep red in color with a pleasant tropical citrus taste. There was no characteristic ibuprofen taste or throat bite. The solution was stable for a month at temperatures from −5° C. to +45° C. The molar ratio of ibuprofen to hydroxypropyl beta cyclodextrin was 1 to 1.61 and the weight ratio Was 1:12.

EXAMPLES 2 AND 3

An ibuprofen formulation in accordance with this invention was prepared additionally containing pseudoephedrine hydrochloride and in Example 3 additionally containing both pseudoephedrine hydrochloride and dextromethorphan hydrobromide, as follows:

| Ingredients | Example 2 % W/V | Example 2 g/200 ml | Example 3 % W/V | Example 3 g/200 ml |
|---|---|---|---|---|
| Part I | | | | |
| Purified Water Deionized, USP | 24.00 | 48.00 | 24.00 | 48.00 |
| Hydroxpropyl-Beta-Cyclodextrin (D.S. = 7) | 24.00 | 48.00 | 24.00 | 48.00 |
| Ibuprofen, USP | 2.00 | 4.00 | 2.00 | 4.00 |
| Part II | | | | |
| Purified Water Deionized, USP | 19.00 | 38.00 | 19.00 | 38.00 |
| Sodium Benzoate, NF | 0.25 | 0.50 | 0.25 | 0.50 |
| Sodium Saccharin, USP | 0.25 | 0.50 | 0.25 | 0.50 |
| Disodium Edetate, USP | 0.05 | 0.10 | 0.05 | 0.10 |
| Sucrose, NF | 38.00 | 76.00 | 38.00 | 76.00 |
| Glycerin, USP | 10.00 | 20.00 | 10.00 | 20.00 |
| Sorbitol Solution, USP | 10.00 | 20.00 | 10.00 | 20.00 |
| Part III | | | | |
| Dextromethorphan HBr | — | — | 0.15 | 0.30 |
| Pseudoephedrine HCl | 0.30 | 0.60 | 0.30 | 0.60 |
| FD & C Blue #1 (0.1% W/V Aq Soln) | 0.15% v/v | 0.30 ml | 0.15% v/v | 0.30 ml |
| FD & C Red #40 (10% W/V Aq Soln) | 0.47% v/v | 0.94 ml | 0.47% v/v | 0.94 ml |
| Tropical Citrus Flavor | 0.30 | 0.60 | 0.30 | 0.60 |
| Purified Water Deionized, USP | q.s. to 100 ml | q.s. to 200 ml | q.s. to 100 ml | q.s. to 200 ml |

A 48 gram portion of the water was weighed into a first beaker fitted with a Lightnin mixer and steam bath and the hydroxypropyl beta cyclodextrin was added and dissolved therein. The ibuprofen was added to the cyclodextrin solution and the batch was heated to 50° C. with mixing. Mixing was continued for 30 minutes while maintaining the 50° C. temperature and the solution was then cooled to 25° C. with mixing.

Into a separate beaker fitted with a Lightnin mixer and a steam jacket 38 grams of water were added and there were dissolved therein with mixing the sodium benzoate, the sodium saccharin and the disodium edetate while heating to 70°14 75° C. The sucrose was added with mixing and the 70°–75° C. temperature was maintained for fifteen minutes. The solution was cooled to 25° C. with mixing.

To this batch in the second beaker were added and dissolved therein the glycerin, the sorbitol solution, the dextromethorphan hydrobromide, the pseudoephedrine hydrochloride, the ibuprofen/cyclodextrin solution from the first beaker, the flavor and the color solutions, and mixed for 10 minutes after the last addition. Then the volume was adjusted to 200 milliliters with water and mixed for an additional 5 minutes.

The final solutions were a clear, deep red in color, pleasant tasting with a sweet/tart tropical citrus flavor with no bitter ibuprofen taste or throat bite. Example 3 exhibited a slight bitterness characteristic of dextromethorphan hydrobromide which can be overcome with more sweetener.

The final solutions had a pH of 4.50 and 4.46 respectively and each had a molar ratio of ibuprofen to hydroxypropyl beta cyclodextrin of 1.1.61 and a weight ratio of 1:12. The solutions were stable for one month at temperatures from −5 to +45° C.

EXAMPLE 4

An ibuprofen formulation in accordance with this invention was prepared additionally containing pseudoephedrine hydrochloride and diphenhydramine hydrochloride as follows:

| Ingredients | % W/V | g/200 ml |
|---|---|---|
| Part I | | |
| Purified Water Deionized, USP | 24.000 | 48.00 |
| Hydroxypropyl-Beta-Cyclodextrin (D.S. = 7) | 24.000 | 48.00 |
| Ibuprofen, USP | 2.000 | 4.00 |
| Part II | | |
| Purified Water Deionized, USP | 19.000 | 38.00 |
| Sodium Benzoate, NF | 0.250 | 0.50 |
| Sodium Saccharin, USP | 0.250 | 0.50 |
| Disodium Edetate, USP | 0.050 | 0.10 |
| Sucrose, NF | 38.000 | 76.00 |
| Glycerin, USP | 10.000 | 20.00 |
| Sorbitol Solution, USP | 10.000 | 20.00 |
| Part III | | |

| Ingredients | % W/V | g/200 ml |
| --- | --- | --- |
| Pseudoephedrine HCl | 0.300 | 0.60 |
| Diphenhydramine HCl | 0.125 | 0.25 |
| FD & C Blue #1 (0.1% W/V Aq Soln) | 0.15% v/v | 0.30 ml |
| FD & C Red #40 (10% W/V Aq Soln) | 0.47% v/v | 0.94 ml |
| Tropical Citrus Flavor | 0.300 | 0.60 |
| Purified Water Deionized, USP | q.s to 100 ml | q.s. to 200 ml |

The procedure was the same in Examples 2 and 3 above and the final solution had similar characteristics except that it had a pH of 4.48.

EXAMPLE 5

An ibuprofen formulation in accordance with this invention was prepared as follows:

| Ingredients | % W/V | g/500 ml |
| --- | --- | --- |
| Part I | | |
| Purified Water Deionized, USP | 20.00 | 100.00 |
| Hydroxypropyl-Beta-Cyclodextrin (D.S. = 7) | 22.00 | 110.00 |
| Ibuprofen, USP | 2.00 | 10.00 |
| Part II | | |
| Purified Water Deionized, USP | 12.25 | 61.25 |
| Sodium Benzoate, NF | 0.25 | 1.25 |
| Sodium Saccharin, USP | 0.25 | 1.25 |
| Disodium Edetate, USP | 0.05 | 0.25 |
| Sucrose, NF | 45.00 | 225.00 |
| Glycerin, USP | 10.00 | 50.00 |
| Sorbitol Solution, USP | 10.00 | 50.00 |
| Part III | | |
| Tropical Citrus Flavor | 0.30 | 1.50 |
| FD & C Red #40 (1% W/V Aq. Soln) | 1.20% v/v | 6.00 ml |
| FD & C Blue #1 (0.1% w/v Aq. Soln) | 0.04% v/v | 0.20 ml |
| D & C Red #33 (1% w/v Aq. Soln) | 0.40% v/v | 2.00 ml |
| Purified Water Deionized, USP | q.s. to 100 ml | q.s. to 500 ml |

The procedure was the same as Example 2 except that (a) 71.25 grams of water were added to the second beaker, including an additional 10 grams to compensate for evaporation, (b) the water was heated to 80°–85° C. prior to sucrose addition, (c) the sucrose solution in the second beaker was cooled to 60° C. prior to adding the glycerin, sorbitol solution and the ibuprofen/cyclodextrin solution from the first beaker, and (d) the batch was cooled to 25°∧ C. prior to adding the color and flavor.

The final product had a pH of 4.63 and was a clear, cherry red solution. It had a sweet, tart, pleasant tasting tropical fruit flavor with no characteristic ibuprofen taste or throat bite. It was stable for 1 month at temperatures from −5° C. to 45° C. The ibuprofen to hydroxypropyl beta cyclodextrin molar ratio was 1:1.47 and the weight ratio was 1:11.

EXAMPLE 6

An ibuprofen formulation containing 5% weight by volume ibuprofen in accordance with this invention was prepared as follows:

| Ingredients | % W/V | g/500 ml |
| --- | --- | --- |
| Part I | | |
| Purified Water Deionized, USP | 42.00 | 84.00 |
| Hydroxypropyl-Beta-Cyclodextrin (D.S. = 7) | 55.00 | 110.00 |
| Ibuprofen, USP | 5.00 | 10.00 |
| Part II | | |
| Purified Water Deionized, USP | 6.00 | 12.00 |
| Sucrose, NF | 20.00 | 40.00 |
| Part III | | |
| Purified Water Deionized, USP | q.s. to 100 ml | q.s. to 200 ml |

An 84 gram portion of the water was weighed into a first beaker fitted with a Lightnin mixer and steam bath and the hydroxypropyl beta cyclodextrin was added in 10 gram increments and dissolved therein. The ibuprofen was added to the cyclodextrin solution and the batch was heated to 50° C. with mixing. Mixing was continued for 30 minutes while maintaining the 50° temperature and the solution was then cooled to 25° C. with mixing. The solution was clear and occupied 160 ml of the desired 200 ml end product.

A sucrose solution was prepared by placing 461 grams of water in a jacketed Hobart Bowl fitted with a Lightnin mixer and heating it to 80°–85° C. The sucrose was added to the hot water while mixing until all had dissolved. The specific gravity was 1.3458 at 85° C., i.e. 50 ml weighed 67.24 grams.

The sucrose solution in the amount of 52 grams was added to the first beaker containing the cyclodextrin-/ibuprofen solution while mixing and additional water was added to make 200 ml. Mixing was continued for 15 minutes and the solution was allowed to cool to 25° C. with mixing.

The final solution had a ph of 3.58 and was clear and colorless. It had a specific gravity of 1.29. The solution had a sweet/sour taste characteristic of an acid which could be masked with a flavoring agent or more sweetener. The ibuprofen to hydroxypropyl beta cyclodextrin weight ratio was 1:11 and the molar ratio was 1:1.47.

It has been found that ibuprofen to hydroxypropyl beta cyclodextrin weight ratios of less than 1:11, using a hydroxypropyl beta cyclodextrin having a degree of substitution of 7, produces an unstable solution even upon mixing at elevated temperature because a precipitate forms on cooling to room temperature. Even after filtration through #41 Whatman filter paper at room temperature, additional precipitate formed upon further cooling. Such instability is undesirable in a pharmaceutical product. Ibuprofen to hydroxypropyl beta cyclodextrin weight ratios of greater than 1:15 serve no useful purpose and are uneconomical.

The pH of the solutions upon formation will ordinarily be between 3 and 5 but, if not, can be adjusted with, for example, citric acid or an appropriate base.

Ibuprofen solutions having an ibuprofen content of less than about 2% weight ibuprofen by volume of the final composition are less desirable because they are too dilute to provide a normally effective pediatric dose of ibuprofen per teaspoon (per 5 ml) of solution. Similarly, solutions having an ibuprofen content greater than about 5% weight ibuprofen by volume of solution are too strong and require dilution to provide a normally effective adult dose of ibuprofen per teaspoon (per 5 ml) of solution.

We claim:

1. A palatable aqueous base ibuprofen solution suitable for oral administration having a pH of about 3 to 5 comprising about 2% to 5% weight ibuprofen by volume of the total composition, about 20% to about 70% weight by volume of at least one taste masking sweetening ingredient and about 22% to about 75% weight by volume of hydroxypropyl beta cyclodextrin having a degree of hydroxpropyl substitution of about 6 to about 7.5, the weight ratio of ibuprofen to hydroxypropyl beta cyclodextrin being 1:11 to 1:15, and water qs to 100% by volume of the composition.

2. The palatable aqueous base ibuprofen composition of claim 1 containing about 2% weight ibuprofen by volume of the total composition and additionally containing about 0.30% weight by volume of pseudoephedrine hydrochloride.

3. The palatable aqueous base ibuprofen composition of claim 2 additionally containing about 0.15% weight by volume of dextromethorphan hydrobromide.

4. The palatable aqueous base ibuprofen composition of claim 2 additionally containing about 0.125% weight by volume of diphenhydramine hydrochloride.

5. The palatable aqueous base ibuprofen composition of claim 1 wherein the taste masking sweetening ingredient is selected from the group consisting of at least one of sodium saccharin, aspartame, sucrose, glycerin, sorbitol, and sorbitol solution.

* * * * *